(12) United States Patent
Manassen

(10) Patent No.: US 9,618,448 B2
(45) Date of Patent: Apr. 11, 2017

(54) GRAZING ORDER METROLOGY

(71) Applicant: KLA-Tencor Corporation, Milpitas, CA (US)

(72) Inventor: Amnon Manassen, Haifa (IL)

(73) Assignee: KLA-Tencor Corporation, Milpitas, CA (US)

(*) Notice: Subject to any disclaimer, the term of this patent is extended or adjusted under 35 U.S.C. 154(b) by 14 days.

(21) Appl. No.: 14/706,343

(22) Filed: May 7, 2015

(65) Prior Publication Data
US 2015/0233818 A1 Aug. 20, 2015

Related U.S. Application Data

(63) Continuation of application No. PCT/US2015/014491, filed on Feb. 4, 2015.
(Continued)

(51) Int. Cl.
*G02B 5/18* (2006.01)
*G01N 21/41* (2006.01)
(Continued)

(52) U.S. Cl.
CPC ......... *G01N 21/41* (2013.01); *G03F 7/70633* (2013.01); *G03F 7/70683* (2013.01); *G06F 17/50* (2013.01); *G01N 2201/061* (2013.01)

(58) Field of Classification Search
CPC .............................. G02B 5/18; G02B 5/1847
See application file for complete search history.

(56) References Cited

U.S. PATENT DOCUMENTS 6,917,471 B2 * 7/2005 Shiozaki .................. G01J 3/02
359/558
8,319,966 B2 11/2012 Zawaideh et al.
(Continued)

FOREIGN PATENT DOCUMENTS

WO WO2013/169791 11/2013
WO WO2013/186136 12/2013
WO WO2014/011565 1/2014

OTHER PUBLICATIONS

Böwering, N.R., J. R. Hoffman, O. V. Khodykin, C. L. Rettig, B. A. M. Hansson, A. I. Ershov, I.V. Fomenkov. "Metrology of laser-produced plasma light source for EUV lithography," https://www.cymer.com/files/pdfs/Technology/2005/Metrology_of__EUV_Lithography.PDF.
(Continued)

Primary Examiner — Jonathan Hansen
(74) Attorney, Agent, or Firm — Suiter Swantz pc llo

(57) ABSTRACT

Metrology targets, optical systems and methods are provided, which enable metrology measurements of very small features, using resonance of illuminated radiation within periodical structures of the target, under appropriate illumination. Metrology targets comprise periodical structure(s) configured to resonate incident radiation and having a pitch defined by the grating equation with respect to configured parameters such as the selected diffraction order, refractive indices and the illumination's wavelength(s) and incidence angles. Possibly, the target may further comprise substructure(s) which are optically coupled with the resonating incident radiation in the periodical structure(s). The spatial organization of the periodic structures and the substructures, as well as the optical organization of illuminated and scattered radiation provide collecting phase signals from the targets at a range of parameters, such as different wave-
(Continued)

lengths, spatial angles and polarizations to enhance the metrology signal and achieve a very high sensitivity to very small target features.

17 Claims, 11 Drawing Sheets

Related U.S. Application Data

(60) Provisional application No. 61/936,233, filed on Feb. 5, 2014.

(51) Int. Cl.
*G06F 17/50* (2006.01)
*G03F 7/20* (2006.01)

(56) References Cited

U.S. PATENT DOCUMENTS

| | | |
|---|---|---|
| 2005/0079635 A1 | 4/2005 | Norman |
| 2005/0213886 A1 | 9/2005 | Balakrishnan et al. |
| 2008/0013176 A1* | 1/2008 | Wang .............. G02B 5/18 359/566 |
| 2012/0039568 A1 | 2/2012 | Feng |
| 2013/0222795 A1 | 8/2013 | Madsen et al. |
| 2013/0258310 A1 | 10/2013 | Smilde et al. |

OTHER PUBLICATIONS

Nowak, Stanisław H. "Investigation of surface nanostructures with grazing angle x-ray fluorescence techniques." http://ethesis.unifr.ch/theses/downloads.php?file=NowakS.pdf, Kielce, Poland, 2012.

Hofmann, T., E. Dobisz, and B. M. Ocko. "Grazing incident small angle x-ray scattering: A metrology to probe nanopatterned surfaces", http://scitation.aip.org/content/avs/journal/jvstb/27/6/10.1116/1.3253608,2009.

* cited by examiner

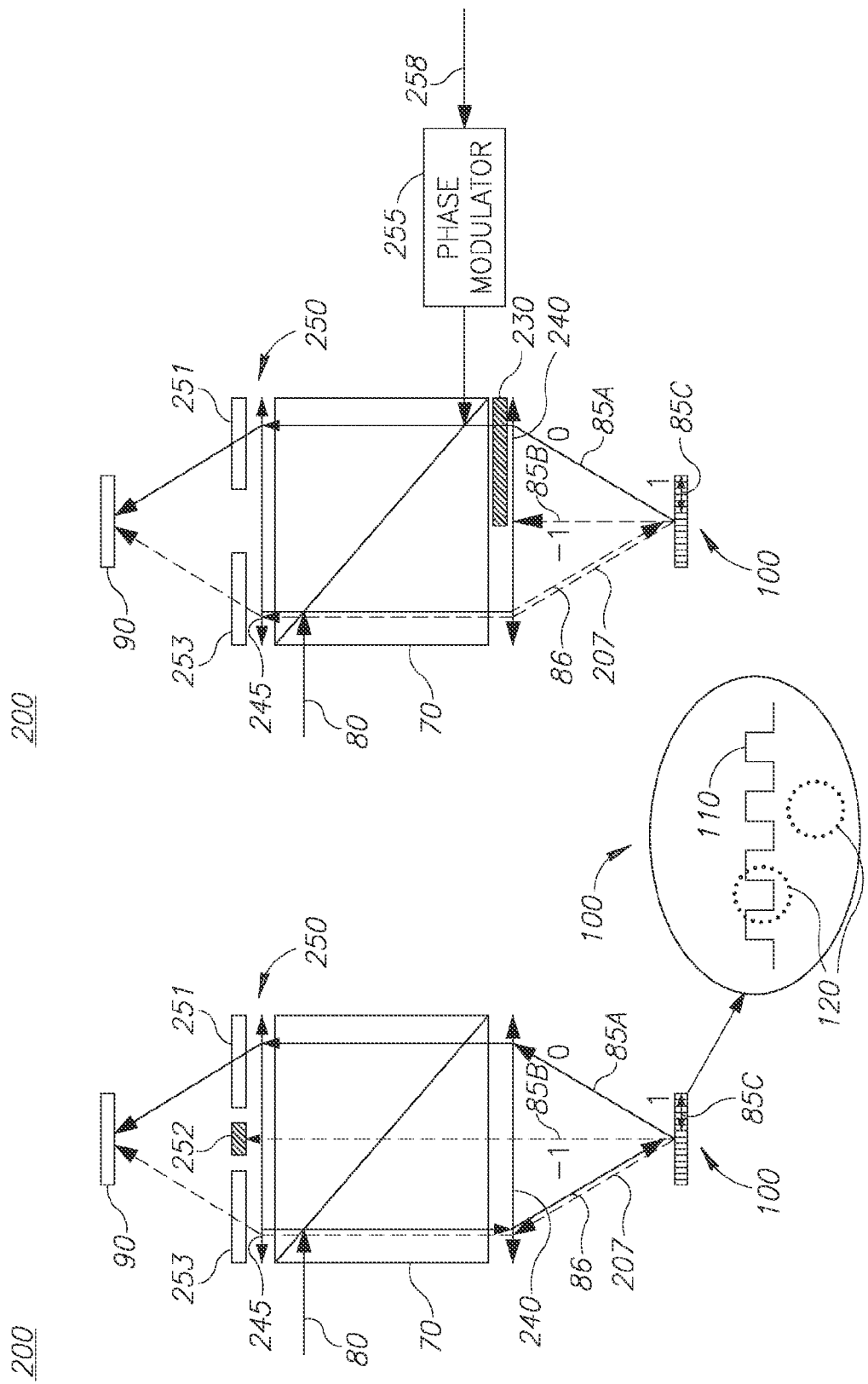

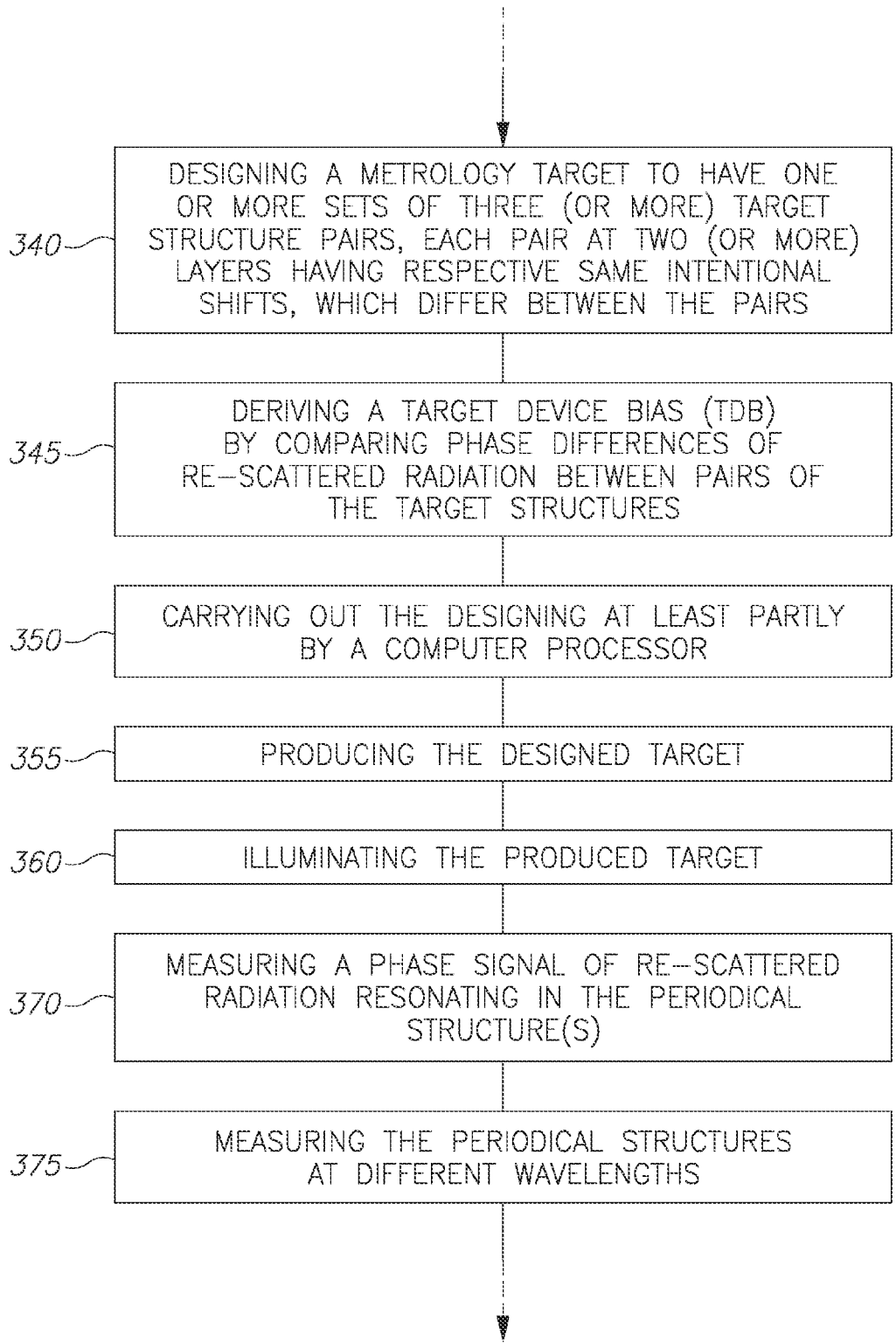
Figure 12 (cont. 1)

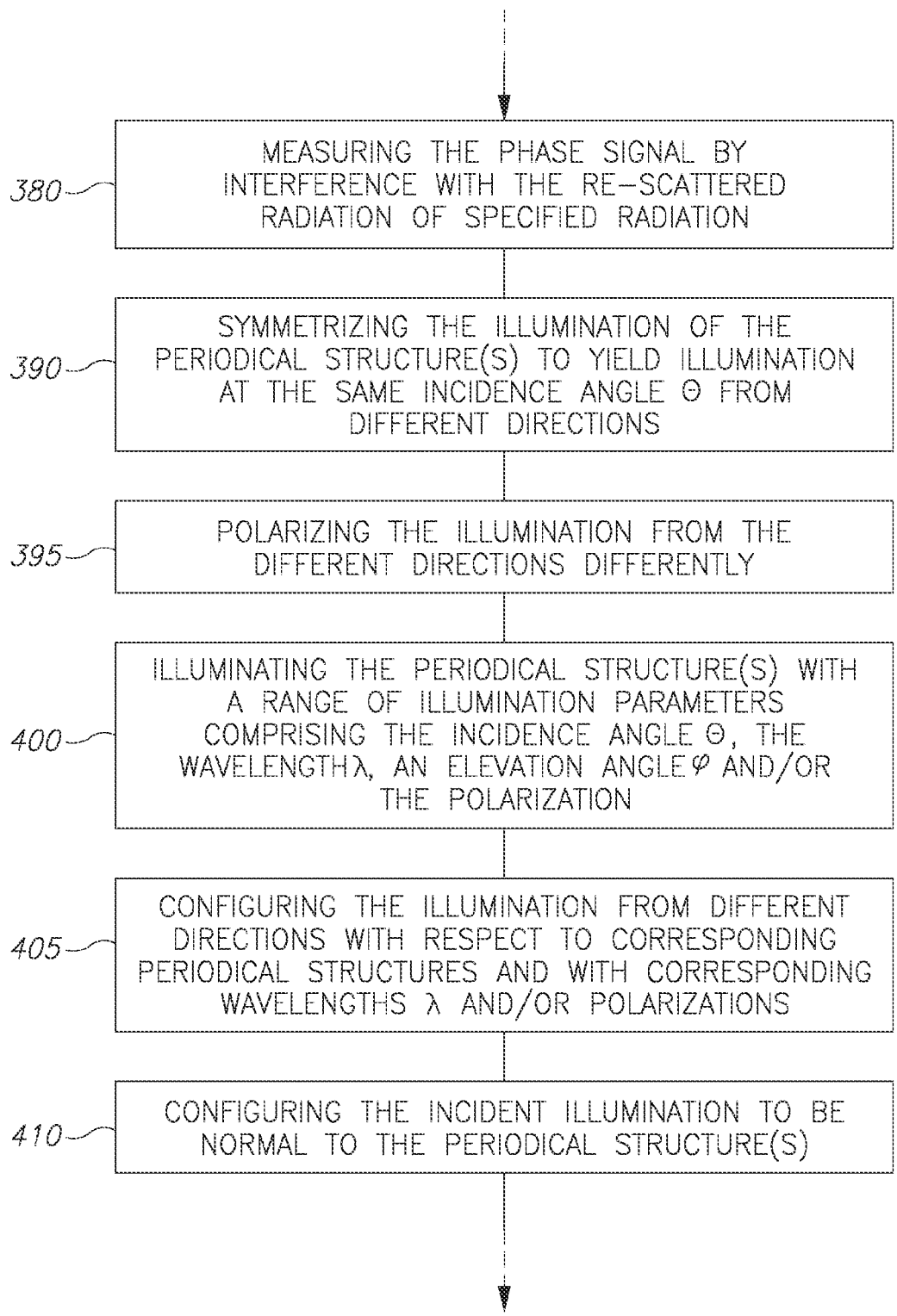
Figure 12 (cont. 2)

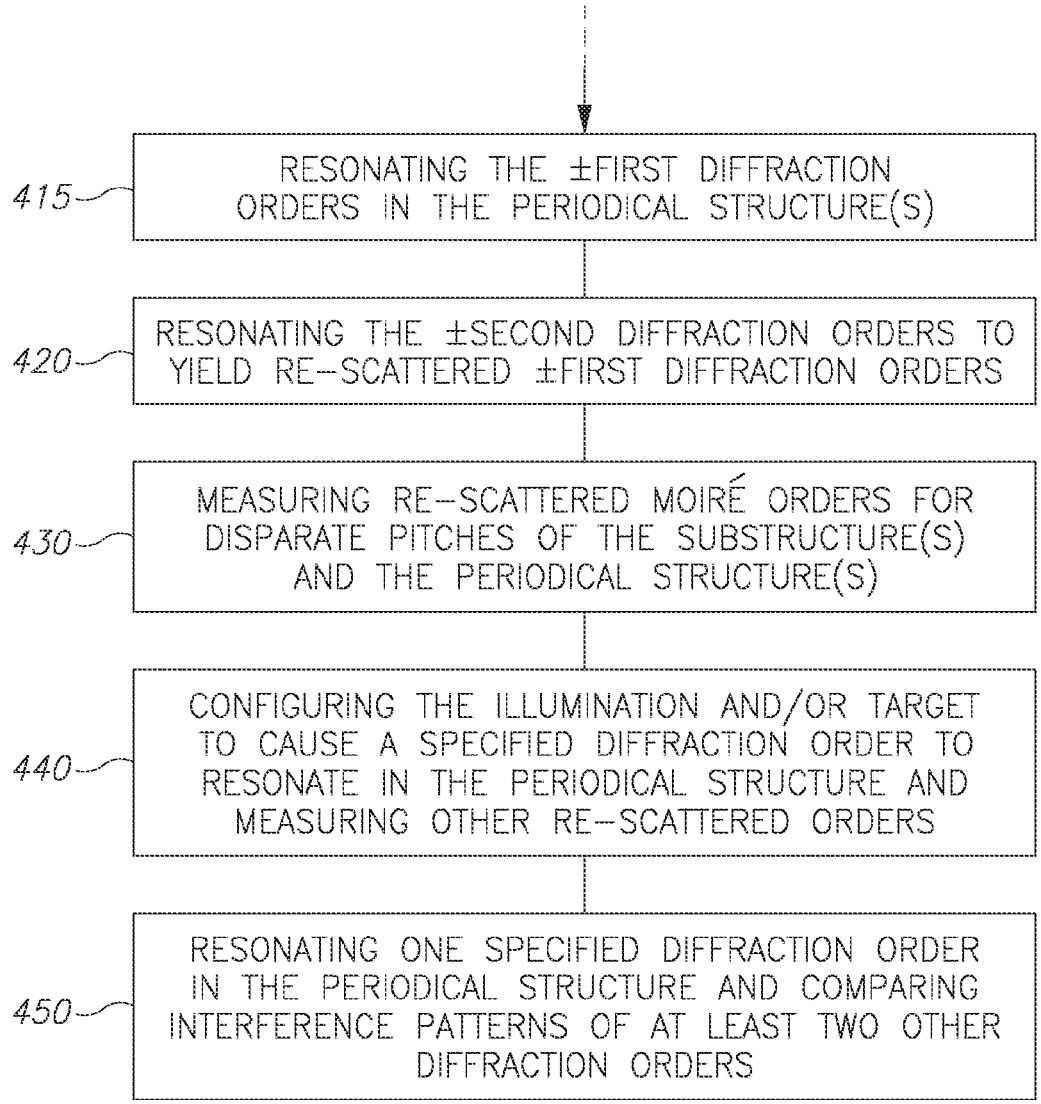
Figure 12 (cont. 3)

GRAZING ORDER METROLOGY

CROSS REFERENCE TO RELATED APPLICATIONS

This application is filed under 35 U.S.C. §111(a) and §365(c) as a continuation of International Patent Application No. PCT/US2015/014491, filed on Feb. 4, 2015, which application claims the benefit of U.S. Provisional Patent Application No. 61/936,233 filed on Feb. 5, 2014, which applications are incorporated herein by reference in their entirety.

BACKGROUND OF THE INVENTION

The present invention relates to the field of metrology, and more particularly, to targets and measurement of very small features, on the scale of device features and quantized substructures.

According to the ITRS (International Technology Roadmap for Semiconductors), the 5 nm technology node will be ramping in about 5 years. Such device dimensions deviate considerably from the typical dimensions of structures used to form targets for overlay metrology. The dimensions of target structures are typically in the 100-1000 nm range. This two orders of magnitude gap leads to a significant bias of a few nanometers between overlay measured on a device and overlay measured from a target. The control budget at these advanced nodes will be just a couple of nanometers, and this target-device bias is becoming a huge issue which prohibits overlay control based on the current methodology.

SUMMARY OF THE INVENTION

One aspect of the present invention provides a metrology target comprising at least one periodical structure configured to resonate incident radiation and having a pitch of $(m\lambda)/(n \sin \theta)$, m being a selected order other than zero, $\lambda$ an illumination wavelength, n a wafer's refractive index and $\theta$ being an incidence angle of the radiation.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 6 is a high level schematic illustration of an optical metrology system in which the phase signal is measured by interfering reflected resonating radiation with attenuated reflected zeroth order, according to some embodiments of the invention.

FIG. 7 is a high level schematic illustration of an optical metrology system in which the phase signal is measured by interfering reflected resonating radiation with coherent, phase modulated radiation, according to some embodiments of the invention.

DETAILED DESCRIPTION OF THE INVENTION

Figure 1:
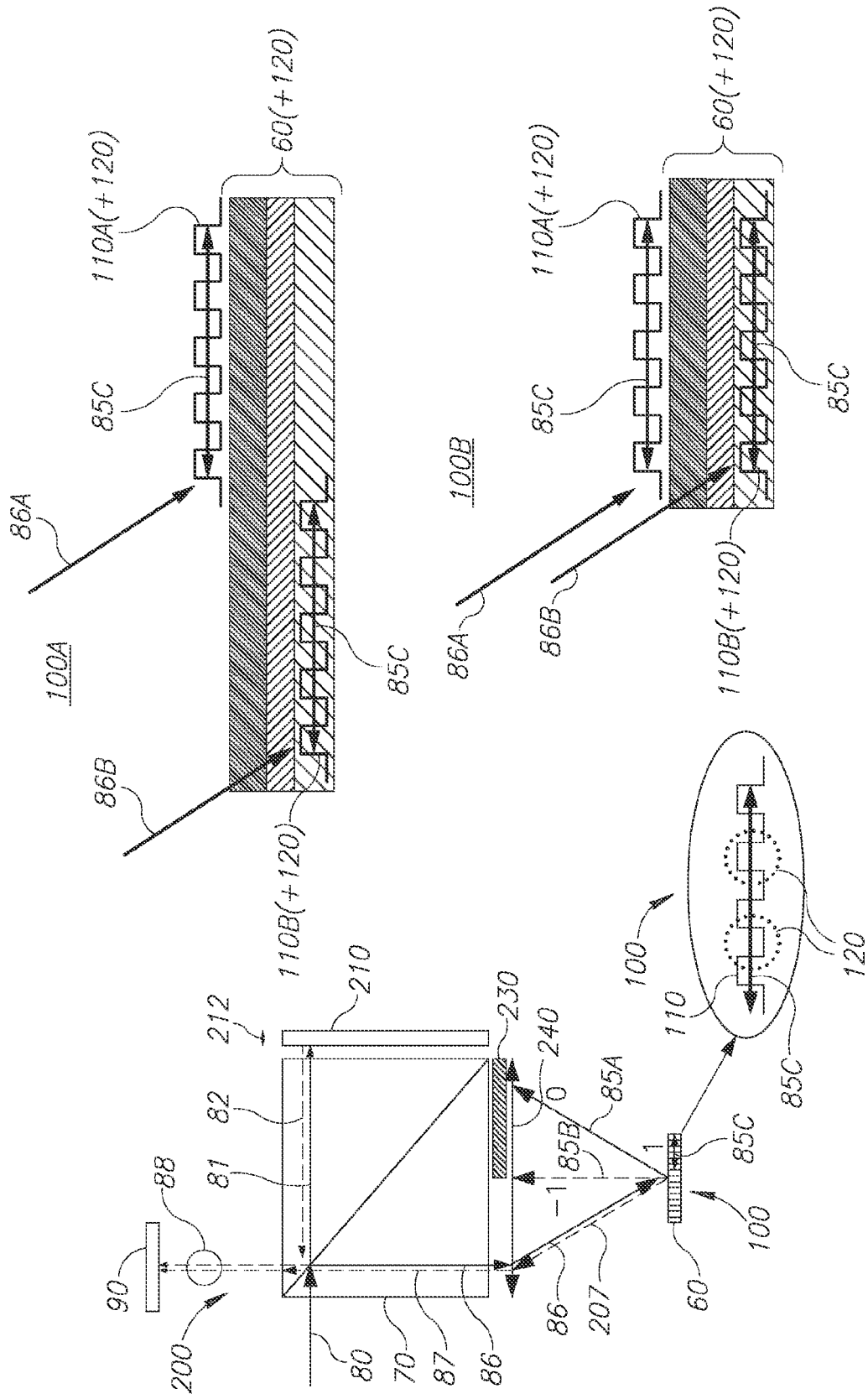
FIG. 1 is a high level schematic illustration of an optical metrology system and respective metrology targets, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Imaging overlay measurement systems are limited by resolution and cannot directly measure targets with nanometer dimensions. Angular and spectral scatterometry methods are used with a model and thus enable measurement of optically unresolved features. However the metrology sensitivity is compromised with target size reduction. While SEM (scanning electron microscopy) could achieve the required resolution, it has a throughput limit, and most subsurface elements are excluded from the reach of the probing electrons.

It is highly desirable to measure device-like targets or even device elements themselves in order to resolve this challenge. The problem of this approach is that the sensitivity of standard optical metrology to overlay (or any other quantity for that matter) of targets consisting of structures of such small dimensions is tiny, and therefore the accuracy of the metrology is severely compromised. The purpose of the proposed disclosure is to enable a significant enhancement of the sensitivity of optical metrology to device-like targets by employing grazing order metrology, namely measurements of radiation which resonates within the measured structures.

Wood's anomalies happen when a scattered order travels in parallel to a grating, for specific wavelengths, angles of incidence and grating pitch values. In such a case, the electromagnetic wave re-scatters over the grating in a way that could change the field of the scattered orders and may also cause some of the energy to backtrack in a direction parallel to the incident angle but with a reversed K vector. The light traveling along the grating could traverse it many times before re-scattering or before affecting scattered orders, exhibiting resonance within the grating. Hence, the interaction of the electromagnetic radiation with intra-grating disturbances intensifies and may therefore result in enhanced sensitivity to any phase disturbance within the grating of the scattered radiation. Since the features composing the nano-targets within the grating are very small, their interaction cross section with electromagnetic radiation is small. This may be overcome by placing many identical nano-structures to intercept the electromagnetic wave more intensively and/or by placing them within a resonant cavity or resonance cavities formed by structures of the grating and/or in the region of the wafer in which the grating is designed.

In the disclosed invention, the interaction cross section between electromagnetic radiation and nano structures is increased by enabling long interaction time or by placing nano-structures, device-like structures or actual devices within the grating. Any change in the nano-structure, and in particular shifts in its position, may lead to a phase change in the re-scattered light or in the scattered orders. Hence, grazing order metrology is employed to enable a significant enhancement of the sensitivity metrology to device like targets.

Metrology targets, optical systems and methods are provided, which enable metrology measurements of very small features, using resonance of illuminated radiation within periodical structures of the target, under appropriate illumination. Metrology targets comprise periodical structure(s) configured to resonate incident radiation and having a pitch defined by the grating equation with respect to configured parameters such as the selected diffraction order, refractive indices and the illumination's wavelength(s) and incidence angles. Possibly, the target may further comprise substructure(s) which are optically coupled with the resonating incident radiation in the periodical structure(s). The spatial organization of the periodic structures and the substructures, as well as the optical organization of illuminated and scattered radiation provide collecting phase signals from the targets at a range of parameters, such as different wavelengths, spatial angles and polarizations to enhance the metrology signal and achieve a very high sensitivity to very small target features.

FIG. 1 is a high level schematic illustration of an optical metrology system 200 and respective metrology targets 100, according to some embodiments of the invention. Optical metrology system 200 is configured to measure a phase signal of reflected radiation 207 resonating in at least one periodical structure 110 (e.g., a grating) having a pitch of $p=(m\lambda)/(n \sin \theta)$, m being a selected order other than zero (e.g., illustrated is order m=1), $\lambda$ an illumination wavelength, n a wafer's refractive index and $\theta$ being an incidence angle of the radiation. Respectively, metrology target 100 comprises at least one periodical structure 110 configured to resonate incident radiation 86 and having a pitch of $p=(m\lambda)/(n \sin \theta)$, m being a selected order other than zero, $\lambda$ an illumination wavelength, n the refractive index of the grating and $\theta$ being an incidence angle of the radiation. In a non-limiting example, periodical structures 110 may have a typical dimension (e.g., a pitch) of 1 micron. In order to get second order grazing conditions of radiation with an incidence angle $\theta_{in}=45°$, the required wavelength is $\lambda=p\cdot\sin(90-\theta_{in})/m=425$ nm. In certain embodiments, the pitch of the grating may be between 100 nm and 1000 nm, and the incidence angles, measured orders and wavelengths may be adapted respectively.

Optical metrology system 200 comprises an illumination 80 split by beam splitter 70 into a beam 86 illuminating (via a lens 240) target 100 on a wafer 60. Periodic structure(s) 110 of target 100 diffract incident illumination 86 into several diffraction orders, e.g., zeroth order (m=0) 85A, −first order (m=−1) 85B and +first order (m=+1) 85C, of which the latter, upon respective configuration of incident illumination 86 ($\lambda$, $\theta$) and of grating parameters (p, n), resonates within periodic structure 110 (resonance represented by arrow 85C in the enlarged view; resonating mode 85C is also termed "grazing mode" and its extension is schematically illustrated in the Figures by double-headed arrows and/or ellipses) and is emitted as signal 207 therefrom back via lens 240 into beam splitter 70.

It is noted that signal 207 may comprise any scattered diffraction order and that the illustrations depicted signal 207 are non-limiting and used for explanation purposes only (term-wise, the term back-scattered radiation in the present disclosure may be replaced by the term re-scattered radiation, with respective spatial design changes in optical system 200). Optical system 200 may be designed to detect any scattered order as signal 207 by applying the respective changes in the optical design. Signal 207 may be scattered in any direction, depending on the designed or selected details of the intra-grating scattering, as discussed above. For example, if intra-grating scattering structures 120 (see details below) have the same pitch as grazing grating 110 itself, then the grazing order re-scattering is into one or few of the grating's scattering orders (e.g., zeroth order, ±first orders or higher orders). If the intra-grating scattering structures 120 have a pitch that is different from the pitch of grazing grating 110, then the grazing re-scattering may occur into Moiré orders (derived from these pitches). If intra-grating scattering structures 120 are distributed randomly or in an order that does not resemble the order of grating structure 110, then the grazing order re-scattering may be in any direction. Optical system 200 may be designed according to the pitches and order of periodic structure 110 and substructures 120 to capture the respective scattered radiation as signal(s) 207, as exemplified below. Multiple detectors 90 may be applied to measure respective multiple re-scattered components and/or their characteristics (e.g., phases by interferometry).

Illumination 80 is split by beam splitter 70 into a beam 81 reflected from an adjustable mirror 210 (arrow 212 represents the adjustment movement) to yield reflected beam 82 to be interfered (88) with signal 87 (being signal 207 within beam splitter 70) and generate the phase signal at one or more detector 90. Zeroth and −first orders 85A, 85B may be blocked by a blocker 230. Optical system 200 may be designed to measure interferometrically any re-scattered order, e.g., by replacing adjustable mirror 210 replaced by a grating or a diffuse mirror to reflect illumination reference 81 in different directions, to be interfered with the respective scattered order or scattered radiation. In such embodiments, scattered radiation in any direction (as explained above) may be measured interferometrically with respect to illumination radiation 81.

In certain embodiments, incident radiation 86 may be S polarized for improved coupling to grazing mode 85C and/or P polarized in cases target 100 has significant topography or possesses a rotational polarization (the latter case discussed below for nano substructures 120 designed to have transitions with certain selection rules). In certain embodiments, incident illumination 86 may be polarized at 45° with respect to either P or S directions. The structural details of periodic structure 110 and substructures 120 may change the polarization direction of the scattered order(s) in the grazing process, resulting in a polarization signal component. Scattered order 207 may be scanned (e.g., with a rotating polarizer) to provide information about the intra-grating scattering phase and modification of polarization. Incident radiation 86 may have any wavelength λ, as long as the corresponding incident angle (θ) (and respective illumination pupil position in the pitch direction of periodic structure 110) supports a grazing order for that wavelength. For example, substructures 120 may have a typical dimension of ca. 10 nm, 5 nm or lower.

In certain embodiments, target 100 comprises at least one substructure 120 which is optically coupled with resonating incident radiation 85C in at least one periodical structure 110. In FIG. 1, substructure(s) 120 is illustrated schematically as a dotted circle, which may comprise any small scale structures, such as at least one device structure, a variable feature of periodical structure(s) 110 (e.g., a process inaccuracy in periodical structure(s) 110), a spatially limited substructure which exhibits quantized states (see below) and so forth. Substructure(s) 120 effect the phase of signal 207 due to the optical coupling with resonating incident radiation 85C in at least one periodical structure 110. Substructure(s) 120 may be located at a same layer as at least one periodical structure 110 (as illustrated e.g., in the enlarged detail at the left side of FIG. 1) and/or substructure(s) 120 may be located at a layer which is lower than at least one periodical structure 110 (as illustrated e.g., in two examples at the right side of FIG. 1, shown as a side view of a cross section of target 100, as are also similar illustrations below). In the latter case, incident radiation 86 is configured to optically couple substructure(s) 120 and periodical structure(s) 110, e.g., by being p-polarized to increase penetration depth (see below), by having wavelength(s) penetrating to respective layer depth, etc. For example, periodical structure(s) may comprise at least two periodical structures 110 at different layers, an upper periodical structure 110A (e.g., a currently deposited resist layer) configured to resonate incident ultraviolet (UV) radiation 86A and a lower periodical structure 110B (e.g. a previously produced process layer) configured to resonate incident infrared (IR) radiation 86B. Substructure(s) 120 may be located at any of the layers of periodical structures 110A, 110B and/or at intermediate layer(s) of wafer 60. As illustrated in FIG. 1, periodical structures 110A, 110B may be adjacent in top view or may be vertically overlapping. Periodical structures 110A, 110B may be optically coupled when jointly used to produce signal 207 or may be optically uncoupled for separate measurement (e.g., by illumination 86A, 86B having different wavelengths). In certain embodiments, substructure(s) 120 may have a pitch that is different from the pitch p of periodical structure(s) 110, to yield re-scattered Moiré orders. Optical system 200 may be configured to measure such re-scattered Moiré orders.

In certain embodiments, optical metrology system 200 may be configured to scan the phase of backscattered (or re-scattered) signal 207 from periodic structure 110 having multiple substructures 120, possibly in different wavelengths and polarizations, and check the phase relative to a reference grating phase from a reference target (not shown). The reference target may e.g., comprise periodical structure 110 without substructures 120 or with other substructures 120 having some intentionally induced property (e.g., intentional overlay).

Phase disturbances in reflected signal 207, caused e.g., by substructure(s) 120 in associated with periodical structure(s) 110 or production inaccuracies in periodical structure(s) 110, may be measured interferometrically. In certain embodiments, optical metrology system 200 may be configured to measure phase signal 207 by interfering (88) signal 87 with reflected radiation 82.

On the right side of FIG. 1, non-limiting examples are presented for overlay measurements between periodical structures 110 at two layers, such as the resist (top) and process (bottom) layer. The optimal measurement polarization, wavelength and corresponding grating pitch may differ between these layers. For instance, targets process features (periodical structure(s) 110B) which are buried under a hard mask layer are often measurable IR radiation to which hard masks are typically transparent, while resist target features (periodical structure(s) 110A) that are external to semiconductor 60 may be best coupled to UV radiation. In such cases, the process layer grazing order may be designed in the IR while the resist grazing order may be designed in UV. Since the grazing order coupling is independent for the different gratings (as examples for periodical structure(s) 110A, 110B), the gratings may be designed to be placed one above the other (and possess different pitch and optimal measurement wavelength and polarization) thus reducing target area, as described in target 100B. The overlay of periodical structure(s) 110A, 110B may be measure accurately with conventional methods such as imaging overlay for target 100A and scatterometry for target 100B.

In certain embodiments, optical metrology system 200 may be configured to illuminate target 100 by incident illumination 86 which is normal to target 100 and periodical structures 110 and configured to resonate the ±first diffraction orders periodical structure(s) 110 or to resonate the ±second diffraction orders in periodical structure(s) 110 to yield re-scattered ±first diffraction orders. In certain embodiments, the incidence angle of incident illumination 86 with respect to target 100 and/or other parameters such as the pitch and wavelengths may be selected to cause any selected diffraction order to graze target 100, i.e., to resonate as radiation 85C in at least one periodical structure 110, and re-scattered radiation may be respectively measured. For example, the incidence angle may be selected so that the third diffraction order constitutes resonating radiation 85C and first and second diffraction orders are also re-scattered and measured.

Figure 2:
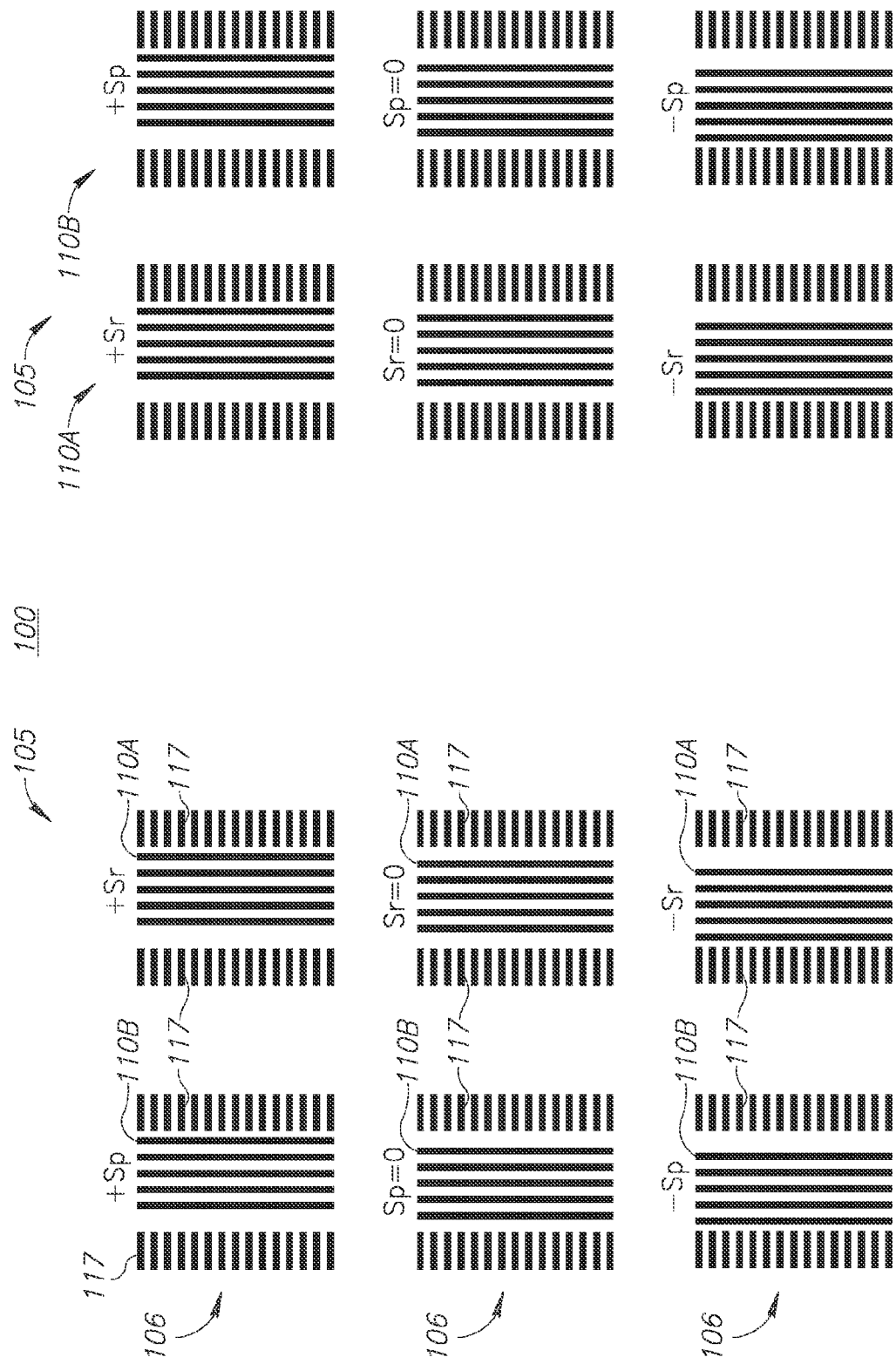
FIG. 2 is a high level schematic illustration of a metrology target for measuring target device bias (TDB), according to some embodiments of the invention.

FIG. 2 is a high level schematic illustration of a metrology target 100 for measuring target device bias (TDB), according to some embodiments of the invention. Metrology target 100 may comprise at least one set 105 of at least three target structure pairs 106, each target structure pair 106 comprising periodical structures 110 at at least two layers (termed in FIG. 2 process –p and resist –r), having a same intentional shift (with respect to adjacent structures 117), wherein the intentional shifts are different among the at least three target structure pairs 106. In the illustration, intentional shifts are denoted by +Sp, +Sr (for the process layer and the resist layer respectively) for one pair 106; 0,0 for another pair 106 and −Sp, −Sr for a third pair 106. It is noted that the term "pair" is used herein as the illustration shows two periodical structures at two layers (process and resist), but does not limit the number of possible layer per "pair", which may also be three or more. The target device bias (TDB) may be calculated from the measured intentional shifts as explained below. Target 100 may comprise two or more similar sets 105 of target structures to support measurement of differential signals for respective pairs 106 between sets 105. A respective target module (not shown) in a metrology system may be configured to derive a target device bias (TDB) from targets 100 by comparing phase differences of reflected radiation between respective pairs 106 in sets 105.

Metrology targets 100 may be designed to solve a target device bias challenge by adding a quantity TDB (Target Device Bias) to the target's overlay in order to correct it and get accurate device overlay. A possible method to resolve the target device bias, includes nano device-like features 120 placed within periodical structures 110 (as illustrated schematically in FIGS. 3, 4A below). For instance three resist gratings 110A and three process gratings 110B may be prepared containing device pitch segmentation. One of resist gratings 110A may contain segmentation with a positive intentional shift +Sr, one resist gratings 110A may contain segmentation with a negative intentional shift −Sr, and one resist gratings 110A may contain segmentation with no intentional shift Sr=0. In the same way, three process gratings 110B may be populated with device pitch segmentations having corresponding +Sp, −Sp and Sp=0 intentional shifts with respect to adjacent structures 117. The re-scattered signal is then measured interferometrically and the following phase differences (±Pp and ±Pr denote respective phase measurements, the indices p and r denoting the respective layers, + and − denote the respective shifts) are calculated as +Pr((+Sr)−(Sr=0)), −Pr((−Sr)−(Sr=0)) for the resist layer structures and respectively +Pp((+Sp)−(Sp=0)), −Pp((−Sp)−(Sp=0)) for the process layer structures.

The effect of the intentional overlay on the phase may then be calibrated for the resist and process layers independently:

CALr=((+Pr)−(−Pr))/(2Sr) and CALp=((+Pp)−(−Pp))/(2Sp).

Then, the shift of the segmentation (device features) relative to gratings 110A, 110B may be calculated using the calibration:

SHIFTr=((+Pr)−(−Pr))/(2CALr) and SHIFTp=((+Pp)−(−Pp))/(2CALp).

Finally the Device Target Bias (TDB) may be calculated as the sum of the calibrations:

TDB=SHIFTr+SHIFTp.

It is noted that this method for calculating the TDB with a differential technique is generic in the sense that it may be used also with conventional imaging in which an unresolved segmentation (not necessarily with substructures 120) is translated relative to a resolved feature with intentional shifts as described in FIG. 2, showing intentional shifts in the X direction in case of cross segmentation targets in which polarization is required to recover the resolved features. Here, the overlay between the intentional shifts may be calculated for calibration and target device bias evaluation as $$TDB = \frac{OVL(+Sr, +Sp) + OVL(-Sr, -Sp)}{OVL(+Sr, +Sp) - OVL(-Sr, -Sp)} \times (Sr + Sp)$$

which can be added to the target overlay OVL(Sr=0, Sp=0). In such a case other quantities such as Symmetry Quality (the average deviation of image harmonics) can be used instead of overlay.

Using grazing order metrology as illustrated in FIG. 1 improves the sensitivity of this approach relative to conventional imaging. Grazing order might also be sensitive enough to intentional shifts of nano targets 120 or device-like targets 120.

Figure 3:
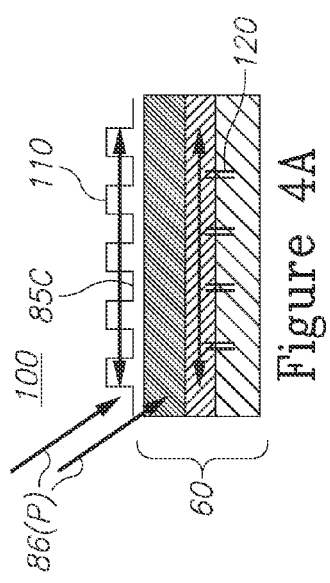
FIG. 3 is a high level schematic illustration of a metrology target having substructures within the periodical structure, according to some embodiments of the invention.

FIG. 3 is a high level schematic illustration of a metrology target 100 having substructures 120 within periodical structure 110, according to some embodiments of the invention. FIG. 3 schematically illustrates a side view of a cross section of target 100. Target 100 may comprise at least one substructure 120 which is optically coupled with resonating incident radiation 85C in at least one periodical structure 110. Incident radiation 86 may be S polarized (denoted as 86(S) in FIG. 3) to limit the spatial extent of resonating radiation 85C to the relevant structures and avoiding interaction with deeper layers of wafer 60. In the illustrated embodiments, only a resist grating 110 may be measured, and the measurements may be used, for example, for focus and dose measurements. Focus and dose sensitive features 120 may be placed within grating 110 and a Focus Exposure Matrix (FEM) with differing training targets may be prepared accordingly. Measured signals may be analyzed by methods such as SRM (Signal Response Metrology). During runs the measured signal may be compared to the FEM for extraction of focus and dose data.

Figure 4A:
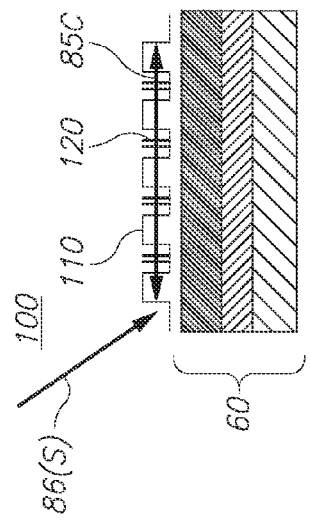
FIGS. 4A-4C are high level schematic illustrations of a metrology target and a respective measurement method, according to some embodiments of the invention.
Figure 4B:
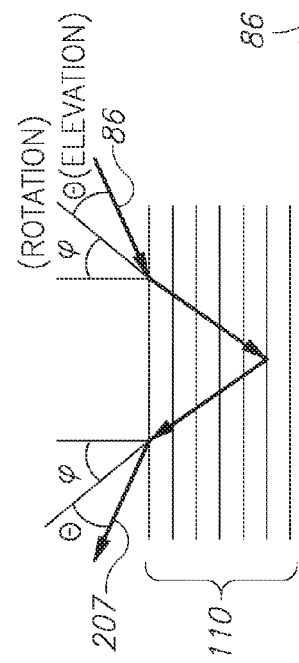
Figure 4C:
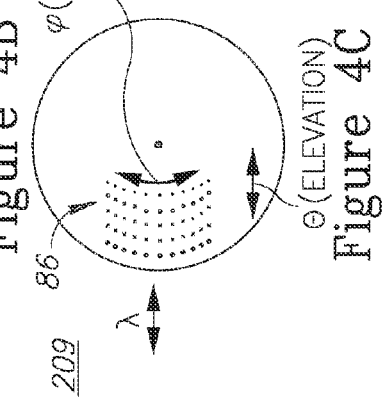

FIGS. 4A-4C are high level schematic illustrations of a metrology target 100 and a respective measurement method 209, according to some embodiments of the invention. FIG. 4A is an example for a metrology target 100 having substructures 120 within wafer 60 below periodical structure 110, yet substructures 120 are optically coupled with resonating incident radiation 85C in periodical structure 110. The optical coupling may be carried out using P polarized radiation 86(P). FIG. 4B is a top view of periodical structure 110 (as a grating) showing incident radiation 86 incoming at an elevation angle θ to the grating and at a side angle φ to the grating, and scattered radiation 207 at respective angles. FIG. 4C is a schematic illustration of the pupil plane signals, e.g., at the illumination pupil, showing ranges of elevation angles (θ), rotation angles (φ) and wavelengths (λ, denoted by different line types) for illumination 86 (respective images may be taken at the pupil plane of the detector, with respect scattered radiation 207, 87). Measurement method 209 may be used for example for model based metrology, to provide many independent measurements to reach an accurate model extraction. In certain embodiments, the illumination angle of incident radiation 86 is inclined at angle φ in a rotational direction relative to periodical structure 110 and elevation angle θ is adjusted to accommodate for the effective grating pitch in the resulting angle according to the grating equation. Varying the parameters of incident radiation 86 causes grazing radiation 85C to probe nano targets as substructures 120 within grating 110 in different angles and thus provides additional structural and phase information. Both angles φ, θ as well as wavelengths λ and polarization configurations may be varied to probe embedded nano targets 120 and may be used in a model based metrology approach.

Measurement method 209 may be applied to targets 100 such as the ones illustrated in FIGS. 4A and 3 but are not limited thereto, and may be used, e.g., for measuring process layer targets 100 within wafer 60. It is noted that FIG. 4A's configuration of the resist serving to create grazing mode 85C while substructures 120 (which are the features to be measured) are within the process layers may be illuminated with P polarization 86(P) in order to increase the interaction cross section between the electromagnetic radiation 86 and the features to be measured (substructures 120).

Advantageously, using grazing order metrology configurations boosts the potential resolution because the grazing order travels in a medium having a higher refractive index than air.

Figure 5:
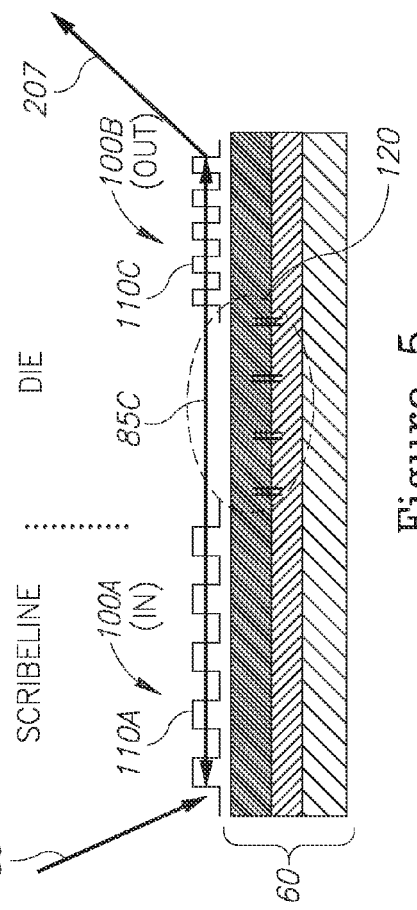
FIG. 5 is a high level schematic illustration of a metrology target having periodical structure(s) optically coupling intermediate device features, according to some embodiments of the invention.

FIG. 5 is a high level schematic illustration of a metrology target 100 having periodical structure 110 optically coupling intermediate device features 120, according to some embodiments of the invention. Periodical structures 110 may comprise at least two periodical structures 110A, 110B interspaced by device features as substructures 120, located either in a same layer as at least two periodical structures 110A, 110B or in a different layer optically coupled therewith. First periodical structure 110A may be configured to optically couple resonating incident radiation 85C with device features 120 and with second periodical structure 110B. Second periodical structure 110B is configured to emit at least a part of coupled resonating radiation 85C. In certain embodiments, target 100 enables measurement of actual device features in the die using periodical structures 110 which are at least partially outside the die, e.g., one of periodical structures 110 may be at the scribeline region. Target 100 may utilize repetitive device features to function as at least one of, or part of periodical structure 110. In certain embodiments, parameters of periodical structures 110A, 110B (e.g., pitch) may be different to enhance the efficiency of introduction and emission of resonating radiation 85C, respectively. In certain embodiments, metrology target 100 may comprise at least two targets 100A(in), 100B(out) having respective periodical structures 110A, 110B and configured to introduce and emit, respectively, resonating radiation 85C as separately designed targets 100A, 100B. The control of the horizontal and vertical extents of resonating radiation 85C may be carried out by configuring parameters and locations of periodical structures 110A, 110B with respect to device features 120 and by configuring incident radiation 86 as described above.

In certain embodiments, the grating (as first, or launch periodical structure 110A) may be used to couple incident electromagnetic radiation 86 into grazing mode 85C and let it propagate parallel to the surface and accumulate information about nano targets 120 placed along its path. An additional grating (as second, or scattering periodical structure 110B) may be placed in order to scatter grazing mode 85C into the collection cone of the optics as scattered radiation 207. For example, large pitch grating 110A may be used to couple light 86 into grazing mode 85C in the scribe line. Resonating radiation 85C then propagates along the devices or nano targets placed in die (as substructures 120) and scattered into the collection optics by second grating 110B, which may have a smaller pitch than launch grating 110A in order to take a smaller in-die area and to decouple the scattered beam from the incident one in the pupil to enable measurement. As grazing order 85C travels in a medium that has an effective refractive index of about 3, the pitch of second grating 110B may be reduced to around 100 nm to reduce the in-die grating size. Grazing order targets 100 may comprise launch and scatter gratings 110A, 110B respectively in different layer interfaces so that propagating grazing order 85C may be used to characterize the interface quality. Using multiple measurement modes as described above (i.e., with varying angles φ, θ, wavelengths λ and polarization configurations) may further enhance information retrieval from device features 120 and/or the layer interfaces. In certain embodiments, grazing order 85C may be used to take advantage of plasmonic effects for metrology. A plasmon is a combined photon-electron mode that travels on surfaces and has wavelengths much shorter than light thus potentially enabling increased resolution. In order to couple into a plasmonic state the electromagnetic wave needs specific conditions which are typically achieved by coupling via Total Internal Reflection (TIR) in prisms. These conditions may be achieved by grazing order 85C as well, for example in a configuration described in FIG. 5. This opens the way to define plasmon sensitive nano targets 120 and benefit from the resolution boost achieved by the short plasmon wavelength. Respective targets 100 and optical systems 200 for measuring targets 100 using plasmonic effects, designed by selecting appropriate substructures 120, are hence part of the present disclosure.

FIGS. 6-9 are high level schematic illustrations of optical metrology systems 200, according to some embodiments of the invention. Optical metrology systems 200 are configured to measure the phase signal of reflected resonating radiation 85C in at least one periodical structure 110 having a pitch of $(m\lambda)/(n \sin \theta)$, m being a selected order other than zero, λ an illumination wavelength, n a wafer's refractive index and θ being an incidence angle of the radiation. In certain embodiments, optical metrology system 200 may be configured to measure the phase signal by interfering signal 87 (i.e., signal 207 passing through beam splitter 70) with reflected radiation 82 (i.e., reflected illumination 81) (FIG. 1). In certain embodiments, optical metrology system 200 may be configured to measure the phase signal by interfering signal 87 with any of the following (any thereof having a same wavelength λ as reflected radiation 85C): attenuated reflected zeroth order 85A (e.g., as in FIG. 6), attenuated reflected −m (minus m) order 85B, radiation coherent with incident radiation, phase modulated radiation (e.g., as in FIG. 7). Clearly, in case resonating radiation 85C is introduced as any diffraction order other than +1, respective other diffraction modes may be interfered therewith to derive the phase signal.

FIG. 6 is a high level schematic illustration of optical metrology system 200 in which the phase signal is measured by interfering re-scattered resonating radiation 85C with attenuated reflected zeroth order 85A, according to some embodiments of the invention. Optical metrology system 200 may be configured to measure the relative phase and intensity of re-scattered radiation 207 by interfering it with zero order (possibly attenuated) radiation 85A and obtain thereby an image on detector 90 that may be further analyzed by respective metrology modules (not shown). Optical metrology system 200 may comprise blocker 252 for blocking reflected −m (minus m) order 85B and an attenuator 251 to attenuate reflected zeroth order 85A. System 200 may also comprise an optical element 253 to modify reflected resonating radiation 85C. Blocker 252, attenuator 251 and optical element 253 may e.g., be positioned after relay optics such as tube lens 245. Illumination 80 may be S polarized to control the expansion of resonating radiation 85C in target 100, depending on the sizes and positions of periodical structures 110 (e.g., gratings) and substructures 120 (e.g., device features, embedded nano-scale features, quantized elements, phase changing structures, plasmonic elements and so forth). In such configurations a resolved grating 110 may be imaged and its translation is sensitive to the phase content of back scattered (or re-scattered) beam 207. Advantageously, the grating translation may be measured with imaging overlay techniques that enable measurement of sub-nanometer grating shifts (relative to a reference grating) and thus can be expected to be sensitive to phase subtleties. It is noted that disclosed direct interferometric measurements may be implemented in an imaging configuration in which the relative phase measurement is replaced by imaged grating shift. As stated above, intra-grating scattering by substructures 120 may impact the intensity and phase of the re-scattered grating orders, Moiré orders generated thereby or any other scattering pattern depending on the details of periodic structure 110 and substructures 120. Thus any pupil or field signals of the impacted orders may be considered for measurement (and schematically represented herein as signal 207).

FIG. 7 is a high level schematic illustration of optical metrology system 200 in which the phase signal is measured by interfering reflected resonating radiation 85C with coherent, phase modulated radiation 258, according to some embodiments of the invention. In certain embodiments, reflected zeroth order 85A may be replaced by coherent, phase modulated radiation 258 as the radiation with which reflected resonating radiation 85C is interfered. Possibly, radiation 258 may be split from illumination 80 before it enters beam splitter 70 and phase modulated in a phase modulator 255 to correct for phase changes or to scan signal 87 with respect to its phase. In certain embodiments, the residual diffraction modes (e.g., −1 85B and 0 85A in the illustration) may be blocked by blocker 230, and phase modulated radiation 258 may be attenuated by attenuator 251. Advantageously, system 200 illustrated in FIG. 7 may enhance accuracy, precision and sensitivity by inducing phase scanning e.g., by phase modulator 255) of zeroth order radiation 85A and/or other radiation such as radiation 258 to cause an oscillatory shift of imaged grating 110. The relative phase may be retrieved from the phase of the grating oscillatory translation. Advantageously, the grating translation may be measured with imaging overlay techniques that enable measurement of sub-nanometer grating shifts using phase modulator 255 to determine and anchor the shifts (possibly instead of using a reference target).

In certain embodiments, optical metrology system 200 may be symmetrized to yield illumination of periodical structure(s) 110 at the same incidence angle θ from at least two directions, e.g., from opposite directions.

Figure 8:
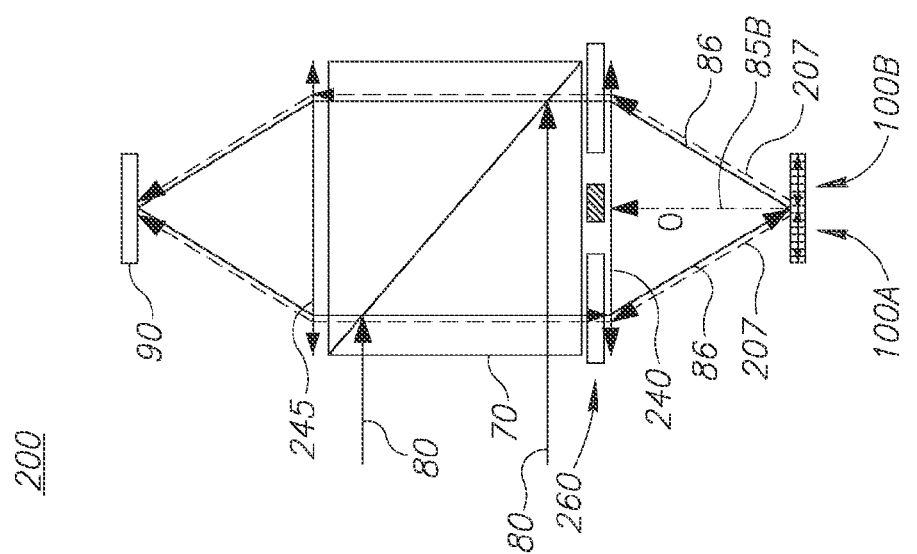
FIG. 8 is a high level schematic illustration of symmetrized optical metrology systems, according to some embodiments of the invention.

FIG. 8 is a high level schematic illustration of symmetrized optical metrology system 200, according to some embodiments of the invention. Any of systems 200 may be symmetrized, i.e., designed with two illumination sources 80 and respective incident radiation 86 and reflected resonating radiation 207, possibly with two symmetrized targets 100A, 100B or target parts; to enhance the measured information. Illumination 80 from different directions may be configured in respect to corresponding periodical structures 110. For example, illumination 80 may be carried out from two symmetric pupil points and system 200 may enable toggling between illumination sources 80 several times per camera frame to integrate or compare the collected data. Blocking (252, 230) and/or attenuation (251, 253) may be carried out by an electro-optical device 260, e.g., a polarization control device, which is configured to participate in the toggling. In certain embodiments, symmetrical and/or symmetrized configurations may be used for standard imaging overlay, e.g., for measuring grating over grating overlays at different colors and respective pitches.

Figure 9:
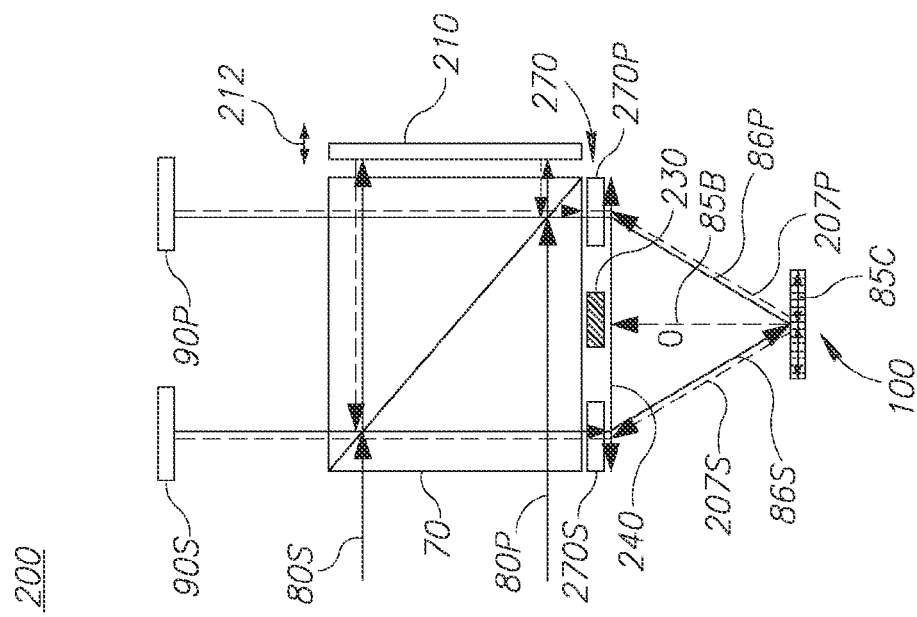
FIG. 9 is a high level schematic illustration of an optical metrology system with multiple polarizations, according to some embodiments of the invention.

FIG. 9 is a high level schematic illustration of optical metrology system 200 with multiple polarizations, according to some embodiments of the invention. Illumination 80 from different directions may be differently polarized. In certain embodiments, different polarizations may be directed through a symmetrized configuration to illuminate target 100 simultaneously or alternatingly by incident radiation 86 with different polarizations. In FIG. 9, such configurations are represented in a non-limiting manner by symmetrized system 200 having a S polarized branch (marked by illumination 80S, S polarizer 270S, incident S polarized illumination 86S, reflected resonating S polarized radiation 207S and detector 90S for S polarized radiation) and a P polarized branch (marked by illumination 80P, P polarizer 270P, incident P polarized illumination 86P, reflected resonating P polarized radiation 207P and detector 90S for P polarized radiation). In certain embodiments, other polarization directions and mixes of polarization directions may be set in any of the branches. Polarizers 270S, P may be part of polarization controlled electro-optical device 270. Adjustable mirror 210 may be used to interfere target scattered radiation with incident (e.g., reflected) radiation to yield respectively polarized phase signals at the respective detectors. Targets 100 may be symmetrized or not, and the directions of illumination as well as other parameters of the illumination may be configured according to specific requirements.

In certain embodiments, illumination 80 may be configured with respect to wavelengths λ and polarizations thereof to yield multiple types of incident radiation 86 on target 100. Optical metrology system 200 may further be configured to periodical structure(s) 110 with a range of illumination parameters comprising at least two of: the incidence angle θ, the wavelength λ, an elevation angle φ and a polarization. In certain embodiments, illumination parameters may span respective ranges of at least three of these parameters. Certain embodiments comprise target design files of any of targets 100. Certain embodiments comprise metrology measurements of targets 100 and/or by systems 200 described herein.

Certain embodiments comprise normal incident illumination 86 in which both the ±first diffraction orders are grazing 85C. In this case no light is reflected to detector 90 as zeroth order 85B is blocked, resulting in increased sensitivity to re-scattering in random directions. Furthermore, intra-grating scattering substructures 120 may have a pitch that is different from the pitch of grating 110 to cause the only information arriving at detector 90 be the Moiré orders. Moreover, grazing orders 85C may be configured to be the ±second diffraction orders, so that upon efficient orders coupling, the scattered events are manifested in the ±first diffraction orders emitted as signal 207 and arriving at detector(s) 90. In certain embodiments, any diffraction order may be configured to resonate within grating(s) 110 and be re-scattered, with appropriate re-scattering of other orders.

In certain embodiments, substructures 120 may be designed to be spatially limited to exhibit quantized states. When device dimensions start to be comparable to the De Broglie wavelength of electrons $\Lambda = h/\sqrt{(2\pi m_e k_B T)}$, which is equal to 4.3 nm at a temperature of 300K, that is in sub-5 nm nodes, electrons in the device are confined to dimensions of the order of the De Broglie wavelength and quantum phenomena such as energy level discretization become important. Small quantum structures can be placed as substructures 120 within measured grating 110 and/or traveling grazing mode path 85C and metrology optical system 200 may couple substructures 120 to resonant scattering from the discrete energy levels to enhance the metrology sensitivity even more. Advantageously, the sensitivity enhancement of targets 100 having substructures 120 which are spatially limited to exhibit quantized states becomes larger for smaller substructures 120. Therefore, the metrology becomes free of the challenge of sensitivity lowering with device shrinking Targets 100 may be designed according to the production processes for the 5 nm and 3 nm nodes and incorporate corresponding periodical structures 110 and respective substructures 120 to benefit from quantum effects.

Figure 10:
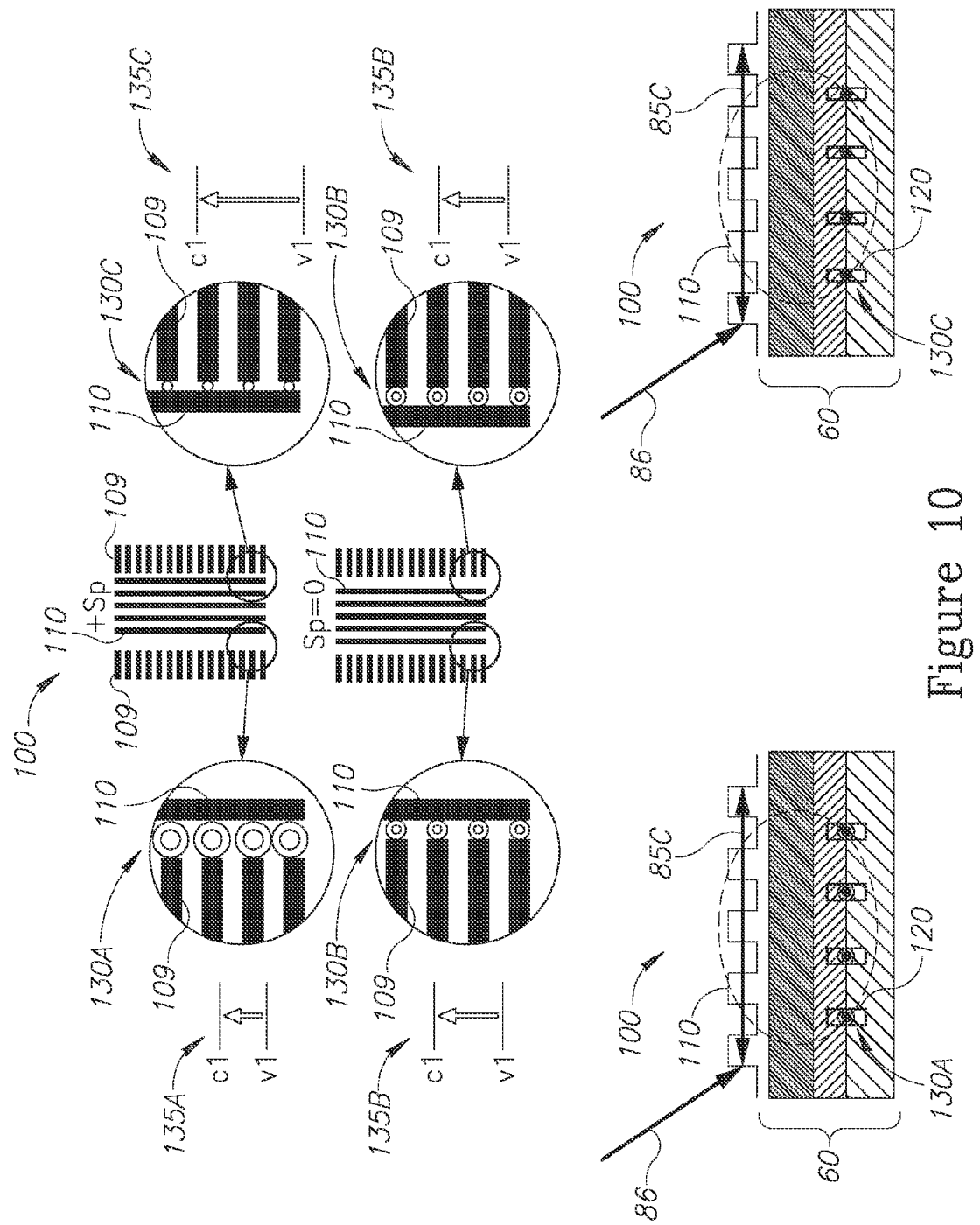
FIG. 10 is a high level schematic illustration of spatially limited substructures exhibiting quantized states, according to some embodiments of the invention.

FIG. 10 is a high level schematic illustration of spatially limited substructures 120 exhibiting quantized states, according to some embodiments of the invention. At the top part of FIG. 10, target 100 is illustrated, in which the spatial limitation is achieved by two perpendicular periodical structures 110, 109 of target 100. The spatial limitation is illustrated by circles 130A, 130B, 130C, e.g., between segmentations of target elements. The confinement areas, when small enough, cause the electrons' wave function to be quantized and thus have associated quantized states for both the conduction and valence band with a characteristic energy transitions marked by a vertical arrow (illustrated as corresponding schematic diagrams 135A, 135B, 135C, with valence and conduction bands labeled v1, c1 respectively). It is further noted, that the quantized states depend on production offsets, as illustrated in FIG. 10. For example, in Sp=0 (no shift), quantization 130B and corresponding transition 135B are symmetric between the left and right edges of periodical structure 110, while in +Sp (shift to the right), the confinement of the right hand edge tightens 130C, resulting in a shift to the blue (larger energy gap) of optical transition 135C while in the left hand edge the confinement relaxes 130A, resulting in a red shift (smaller energy gap) of optical transition 135A. A probe wavelength λ tuned to Sp=0 transition 135B is hence affected by the induced shift +Sp as optical transition 135A, 135C on both sides of periodical structure 110 deviates from the Sp=0 resonance and is accordingly measurable.

In certain embodiments, target designs 100 and optical systems 200 may be configured to measure spatially limited substructures 120 exhibiting quantized states. For example, model based measurements may be conducted with targets shown at the bottom of FIG. 10, according to principles explained above (see FIGS. 4A-4C). For instance, if electrons are confined in CD nano targets, the quantization energy and corresponding optical transitions are be sensitive to the value of the CD. In the right hand side the CD structure 130C is smaller than in the left hand side (130A) and the tighter confined wave function, described by the circles, has more energetic transitions as explained above. Targets 100 may be designed to exhibit quantized optical transitions which are resonant with the wavelength of resist grating grazing order 85C, to manifest any CD deviation as a detectable phase difference by optical systems 200 described above and grazing order methods 300 described below. Furthermore, as optical transitions between quantized states obey transition rules, optical systems 200 may be configured to perform the measurement with circularly polarized illumination 80 having a spin state that matches the designed transition.

Figure 11:
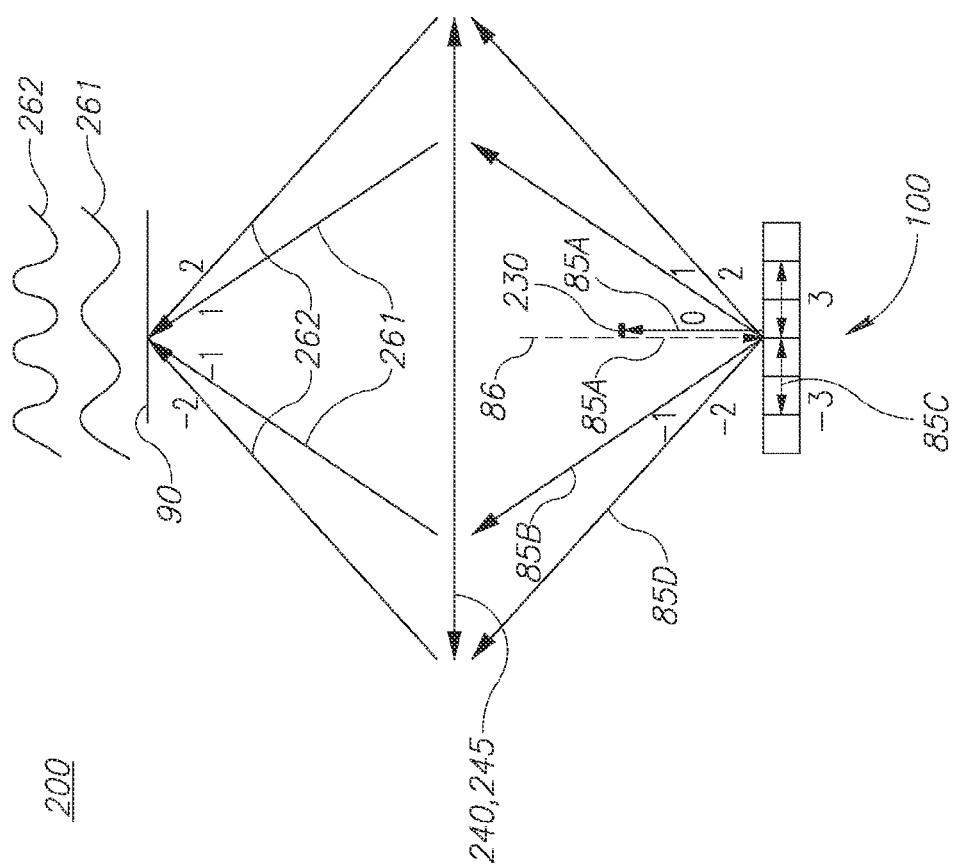
FIG. 11 is a high level schematic illustration of measuring induced parameter changes in re-scattered diffraction orders, according to some embodiments of the invention.

FIG. 11 is a high level schematic illustration of measuring induced parameter changes in re-scattered diffraction orders, according to some embodiments of the invention. In certain embodiments, illumination 86 (as well as grating pitch and illumination wavelengths) may be configured to resonate a specified diffraction order as grazing order 85C in at least one periodical structure 110 and interact with substructures 120. In FIG. 11, the specified diffraction is illustrated in a non-limiting manner as the third diffraction order. Optical system 200 may be configured to interfere re-scattered diffraction orders as schematically demonstrated in FIG. 11 by ±first and ±second orders 85B, 85D respectively and, while blocking reflected zeroth order 85A, interfering the respective orders to yield respective interference patterns 261, 262 at detector 90. The grazing order 85C affects re-scattered orders 85B, 85D to the extent that changes in the interaction between grazing order 85C (e.g., third order) with periodical structure 110 and substructures 120 are manifested in different changes in re-scattered orders 85B, 85D (e.g., first and second orders) such as phase changes or asymmetric amplitude changes, which are measured by interference in optical system 200 as different changes in interference patterns 261, 262. In certain embodiments, optical system 200 may be configured to resonate one specified diffraction order 85C in periodical structure 110 and compare interference patterns 261, 262 of at least two other diffraction orders 85B, 85D.

Figure 12:
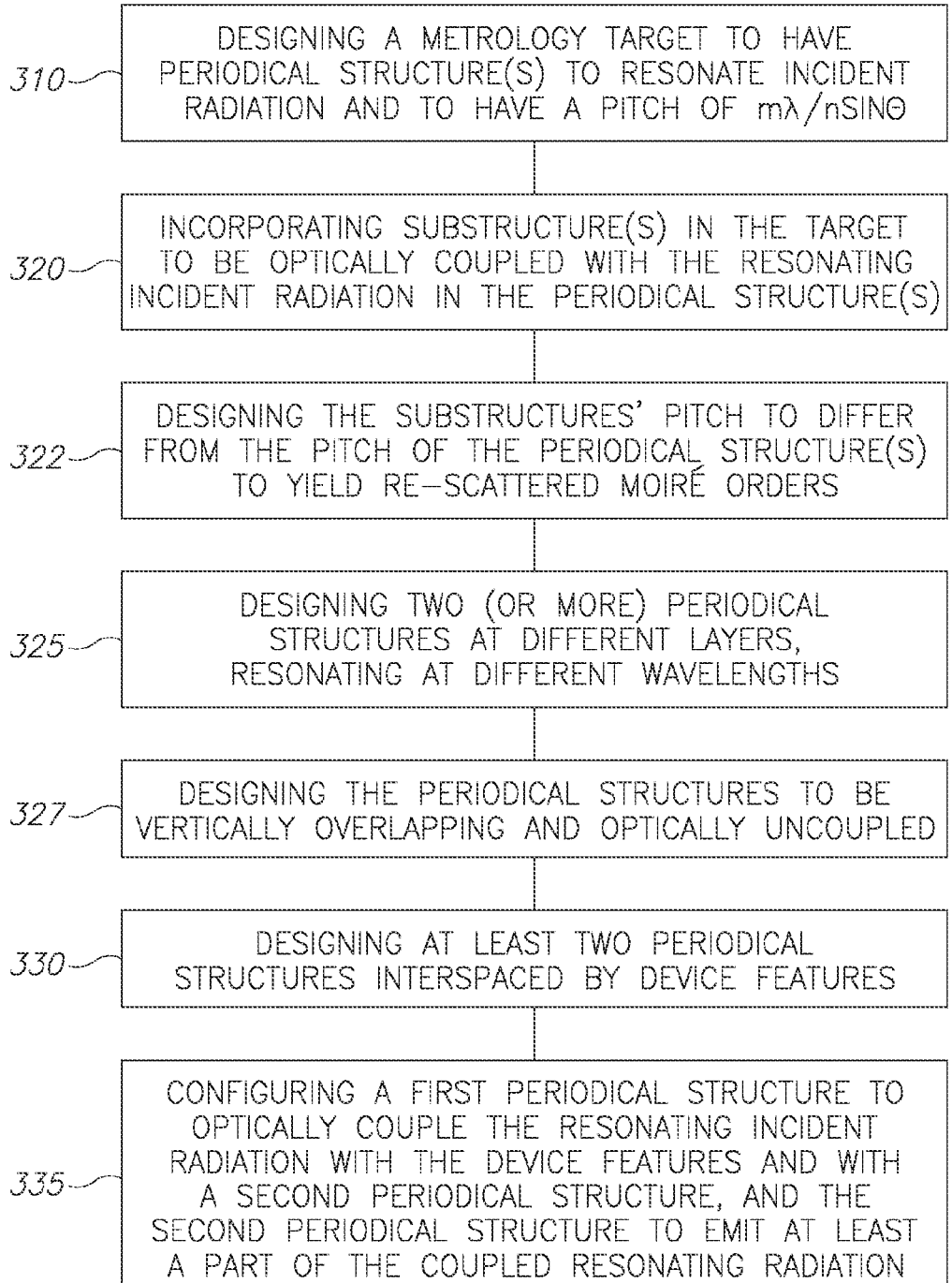
FIG. 12 is a high level schematic flowchart of a method, according to some embodiments of the invention.

FIG. 12 is a high level schematic flowchart of a method 300, according to some embodiments of the invention. Method 300 comprises target design stages, which may at least partially be carried out by computer process(es) as well as production and measurement stages.

Method 300 comprises designing a metrology target to have periodical structure(s) to resonate incident radiation and to have a pitch of mλ/n sin θ (stage 310), with m being a selected order other than zero, λ an illumination wavelength, n a wafer's refractive index and θ being an incidence angle of the radiation. Method 300 may further comprise incorporating substructure(s) in the target to be optically coupled with the resonating incident radiation in the periodical structure(s) (stage 320).

For example, the substructure(s) may comprise at least one device structure. In certain embodiments, the substructure(s) may be spatially limited to exhibit quantized states, e.g., the spatial limitation may be achieved by two perpendicular periodical structures of the target. The substructure(s) may be at a same layer as the periodical structure(s) or at a layer lower than one or more of periodical structure(s) and the incident radiation may be configured to optically couple the substructure(s) and the periodical structure(s). Method 300 may further comprise designing the substructures' pitch to differ from the pitch of the periodical structure(s) to yield re-scattered Moiré orders (stage 322).

In certain embodiments, method 300 may comprise designing two (or more) periodical structures at different layers, resonating different wavelengths (stage 325). Method 300 may further comprise designing the periodical structures to be vertically overlapping and optically uncoupled (stage 327) and/or designing at least two periodical structures interspaced by device features (stage 330).

In certain embodiments, method 300 may comprise configuring a first periodical structure to optically couple the resonating incident radiation with the device features and with a second periodical structure, and the second periodical structure to emit at least a part of the coupled resonating radiation (stage 335).

In certain embodiments, method 300 may comprise designing a metrology target to have one or more sets of three (or more) target structure pairs (each pair may have two or more structures), each pair at two (or more) layers having respective same intentional shifts, which differ between the target structures (stage 340) and deriving a target device bias (TDB) by comparing phase differences of reflected radiation between pairs of the target structures (stage 345). In certain embodiments, the metrology target may be designed to have two separate and similar sets of at least three target structures, to enable measurements of differential signals between corresponding structures in the two sets.

Any of the designing stages may be carried out at least partly by a computer processor (stage 350). Method 300 may further comprise producing the designed target (stage 355) and/or illuminating the produced target, e.g., form one, two or more directions (stage 360) and/or measuring a phase signal of reflected radiation resonating in the periodical structure(s) (stage 370). In certain embodiments, method 300 may further comprise measuring the phase signal by interference with the re-scattered radiation of specified radiation (stage 380). For example, the specified radiation with which the reflected resonating radiation may be interfered may comprise at least one of: attenuated reflected zeroth order, attenuated reflected −m (minus m) order, radiation coherent with incident radiation, phase modulated radiation, any thereof having a same wavelength $\lambda$ as the reflected radiation.

In certain embodiments, method 300 may comprise measuring the periodical structures at different wavelengths (stage 375) and/or polarizing the illumination from the different directions differently (stage 395). For example, the target may comprise an upper periodical structure configured to resonate incident ultraviolet (UV) radiation and a lower periodical structure configured to resonate incident infrared (IR) radiation. In certain embodiments, method 300 may further comprise symmetrizing the illumination of the periodical structure(s) to yield illumination at the same incidence angle $\theta$ from different directions (stage 390), e.g., opposite directions. Method 300 may comprise illuminating the periodical structure(s) with a range of illumination parameters comprising the incidence angle $\theta$, the wavelength $\lambda$, an elevation angle $\phi$ and/or the polarization (stage 400) and/or configuring the illumination from different directions with respect to corresponding periodical structures and with corresponding wavelength $\lambda$ and/or polarization (stage 405). In certain embodiments, illumination with respective ranges may be applied with respect to at least three of the parameters, possibly from different directions.

Method 300 may further comprise configuring the incident illumination to be normal to the periodical structure(s) (stage 410) and resonating the ±first diffraction orders in the periodical structure(s) (stage 415) or resonating the ±second diffraction orders to yield re-scattered ±first diffraction orders (stage 420). Method 300 may further comprise measuring re-scattered Moiré orders for disparate pitches of the substructure(s) and the periodical structure(s) (stage 430), i.e., when substructure(s) in the periodical structure(s) have a different pitch than the pitch of the periodical structure(s). In certain embodiments, method 300 may comprise configuring the incidence angle of the incident illumination (and/or other parameters such as the pitch and wavelengths) to cause a specified diffraction order to resonate in the periodical structure (stage 440). Re-scattered radiation may then me measured and other diffraction orders may be re-scattered at corresponding angles. In certain embodiments, method 300 may further comprise resonating one specified diffraction order in the periodical structure and comparing interference patterns of at least two other diffraction orders (stage 450).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target, comprising:
   at least one periodical structure configured to resonate incident radiation and having a pitch of $(m\lambda)/(n \sin \theta)$, m being a selected order other than zero, $\lambda$ an illumination wavelength, n a refractive index and $\theta$ being an incidence angle of the radiation.

2. The metrology target of claim 1, further comprising:
   at least one substructure which is optically coupled with the resonating incident radiation in the at least one periodical structure.

3. The metrology target of claim 2, wherein the at least one substructure comprises at least one device structure.

4. The metrology target of claim 2, wherein the at least one substructure is at a same layer as the at least one periodical structure.

5. The metrology target of claim 2, wherein the at least one substructure is at a layer which is lower than the at least one periodical structure and the incident radiation is configured to optically couple the at least one substructure and the at least one periodical structure.

6. The metrology target of claim 1, wherein the at least one periodical structure comprises at least two periodical structures at different layers, an upper periodical structure configured to resonate incident ultraviolet (UV) radiation and a lower periodical structure configured to resonate incident infrared (IR) radiation.

7. The metrology target of claim 6, wherein the at least two periodical structure are vertically overlapping and optically uncoupled.

8. The metrology target of claim 1, wherein the at least one periodical structure comprises at least two periodical structures interspaced by device features, and wherein a first periodical structure is configured to optically couple the resonating incident radiation with the device features and with a second periodical structure, and the second periodical structure is configured to emit at least a part of the coupled resonating radiation.

9. The metrology target of claim 2, wherein the at least one substructure is spatially limited to exhibit quantized states.

10. The metrology target of claim 9, wherein the spatial limitation is achieved by two perpendicular periodical structures of the target.

11. The metrology target of claim 2, wherein the at least one substructure has a pitch that is different from the pitch of the at least one periodical structure to yield re-scattered Moiré orders.

12. A method comprising:
designing a metrology target to have at least one periodical structure to resonate incident radiation and to have a pitch of $(m\lambda)/(n \sin \theta)$, m being a selected order other than zero, $\lambda$ an illumination wavelength, n a refractive index and $\theta$ being an incidence angle of the radiation.

13. The method of claim 12, further comprising:
incorporating at least one substructure in the target to be optically coupled with the resonating incident radiation in the at least one periodical structure.

14. The method of claim 12, further comprising:
designing the target to have at least two periodical structures at different layers, an upper periodical structure configured to resonate incident ultraviolet (UV) radiation and a lower periodical structure configured to resonate incident infrared (IR) radiation.

15. The method of claim 14, further comprising:
designing the at least two periodical structures to be vertically overlapping and optically uncoupled.

16. The method of claim 12, further comprising:
designing the at least one periodical structure to comprise at least two periodical structures interspaced by device features; and,
configuring a first periodical structure to optically couple the resonating incident radiation with the device features and with a second periodical structure, and the second periodical structure to emit at least a part of the coupled resonating radiation.

17. The method of claim 13, further comprising:
designing the at least one substructure to have a pitch that is different from the pitch of the at least one periodical structure to yield re-scattered Moiré orders.

* * * * *